(12) United States Patent
Chung et al.

(10) Patent No.: US 6,274,356 B1
(45) Date of Patent: Aug. 14, 2001

(54) **CARBOHYDRATE COMPLEX EXTRACTED FROM *MYCOBACTERIUM TUBERCULOSIS* AND PROCESS FOR THE PREPARATION THEREOF**

(76) Inventors: Tai-Ho Chung, Cheongun Apt. 7-309, #111-1, Daebong-dong, Jung-gu; Chong-Chan Chung, Garden Heights 1st. 101-601, #300, Bumeo 4-dong, Suaeong-gu, both of Daegu (KR)

( * ) Notice: Subject to any disclaimer, the term of this patent is extended or adjusted under 35 U.S.C. 154(b) by 0 days.

(21) Appl. No.: 09/445,662
(22) PCT Filed: Jun. 10, 1997
(86) PCT No.: PCT/KR97/00109
  § 371 Date: Dec. 9, 1999
  § 102(e) Date: Dec. 9, 1999
(87) PCT Pub. No.: WO98/56941
  PCT Pub. Date: Dec. 17, 1998
(51) Int. Cl.[7] ............... C12P 19/04; C12P 1/04; C07H 1/00
(52) U.S. Cl. .............. 435/101; 536/119; 536/123.1; 435/170; 435/253.1; 435/863
(58) Field of Search ............... 435/101, 170, 435/253.1, 863; 536/123.1, 119

(56) References Cited

U.S. PATENT DOCUMENTS

| | | | |
|---|---|---|---|
| 4,329,452 | * 5/1982 | Maruyama | 536/119 |
| 4,394,502 | * 7/1983 | Maruyama | 536/119 |
| 4,746,511 | * 5/1988 | Kobatake et al. | 435/101 |

* cited by examiner

*Primary Examiner*—Herbert J. Lilling
(74) *Attorney, Agent, or Firm*—Anderson Kill & Olick, PC

(57) ABSTRACT

A carbohydrate complex, which is a mixture of low molecular-weight polysaccharides of an arabinomannan structure extracted from *Mycobacterium tuberculosis*, is highly effective in treating various cancer patients without incurring any adverse side effects.

8 Claims, 4 Drawing Sheets

PPM

CARBOHYDRATE COMPLEX EXTRACTED FROM *MYCOBACTERIUM TUBERCULOSIS* AND PROCESS FOR THE PREPARATION THEREOF

FIELD OF THE INVENTION

The present invention relates to a carbohydrate complex extracted from *Mycobacterium tuberculosis*, which has an anticancer activity, and to a process for the preparation thereof.

BACKGROUND OF THE INVENTION

It is generally known that the anticancer activity of *Mycobacterium tuberculosis* is attributable to active agents in the cytoplasmic membrane thereof, particularly the polysaccharide and lipid derivatives.

For instance, Azuma et al. succeeded in isolating N-acetylmuramyl-L-alanyl-D-isoglutamin(MDP) which is an active component of *M. tuberculosis* [Azuma, L. et al., *J. Bact.*, 96, 1885–1887(1968)].

Barnes et al., on the other hand, reported that lipoarabinomannan promotes the production of cytokin [Barnes, P. F. et al., *J. Immunol.*, 149, 541–547(1992)]. Chung et al. isolated from *M. tuberculosis* a substance having an anticancer activity and used this substance, designated as Tubercin-3, in treating terminal-cancer and leprosy patients as well as laboratory animals suffering from tumoral symptoms [Chung, T. H., *J. Korean Med. Ass.*, 17, 427–431 (1974); Chung, T. H. et al., *Yonsei Med. J.*, 17, 131–135 (1976)].

On the other hand, a person infected by *M. tuberculosis* bacilli normally exhibits granulomatous inflammation, and if the infected site is lung, cavity formation progresses together with an inflammatory reaction, induced by secretion of proteins and glycolipids originally present in the cell wall of *M. tuberculosis*. This suggests that, in case high molecular-weight polysaccharides or proteins are used in cancer immunotherapies, it may be difficult to suppress such adverse side effects as undesirable immuno-responses and uncontrollable inflammatory reactions.

SUMMARY OF THE INVENTION

Accordingly, it is an object. of the invention to provide a carbohydrate complex extracted from *Mycobacterium tuberculosis* which has a high anticancer activity and at the same time causes essentially none of the undesirable side-effects mentioned above.

It is another object of the invention to provide a process for the preparation of said carbohydrate complex.

In accordance with one aspect of this invention, there is provided a carbohydrate complex, which is a mixture of polysaccharides extracted from *Mycobacterium tuberculosis*, characterized in that: the polysacchricdes have the molecular weight of below 7,000 and are derived from monosaccharides consisting essentially of mannose, arabinose, glucose and galactose, the monosaccharides forming straight-chain and/or side-chain glycosidic bonds.

In accordance with another aspect of the invention, there is provided a process for the preparation of the carbohydrate complex, comprising the steps of:

(a) culturing *Mycobacterium tuberculosis* in a medium, heating the culture diluted with water at a temperature ranging from 50 to 150° C. under a pressure ranging from 10 to 30 psi and removing bacterial residues from the heated culture solution;

(b) adding an inorganic salt to the remaining solution to form a precipitate and removing the precipitate from the resulting solution;

(c) dialyzing the remaining solution to obtain a dialysis product;

(d) adding an alcohol to the dialysis product to obtain a precipitate, washing the precipitate with an alcohol-ether mixture and extracting the washed, precipitate with an organic solvent; and (e) purifying the extract to obtain the carbohydrate complex.

BRIEF DESCRIPTION OF THE DRAWINGS

The above and other objects and features of the present invention will become apparent from the following description of the invention taken in conjunction with the accompanying drawings, in which.

DETAILED DESCRIPTION OF THE INVENTION

Figure 1:
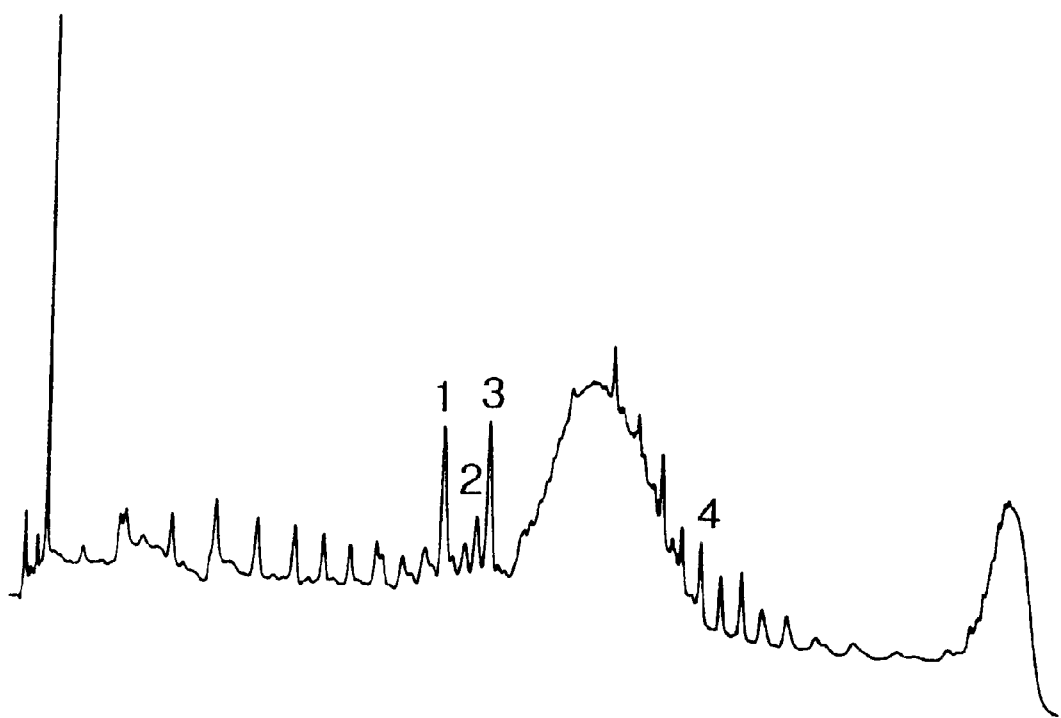
FIG. 1 shows the Bio-LC scan of the hydrolysis product of Tubercin-5 of the present invention (obtained by using a pulsed amperometric detector: pad)
Figure 2:
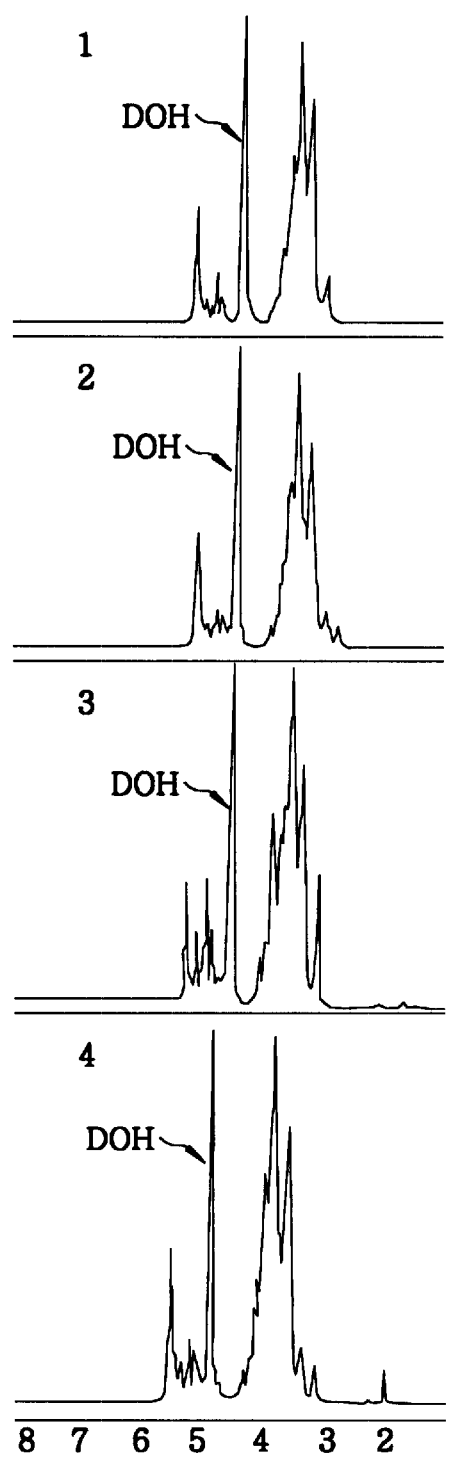
FIG. 2 reproduces $^1$H-NMR scans of the arabinonmannan fractions 1, 2, 3 and 4 which are taken from the hydrolysis product of Tubercin-5 of the present invention.
Figure 3:
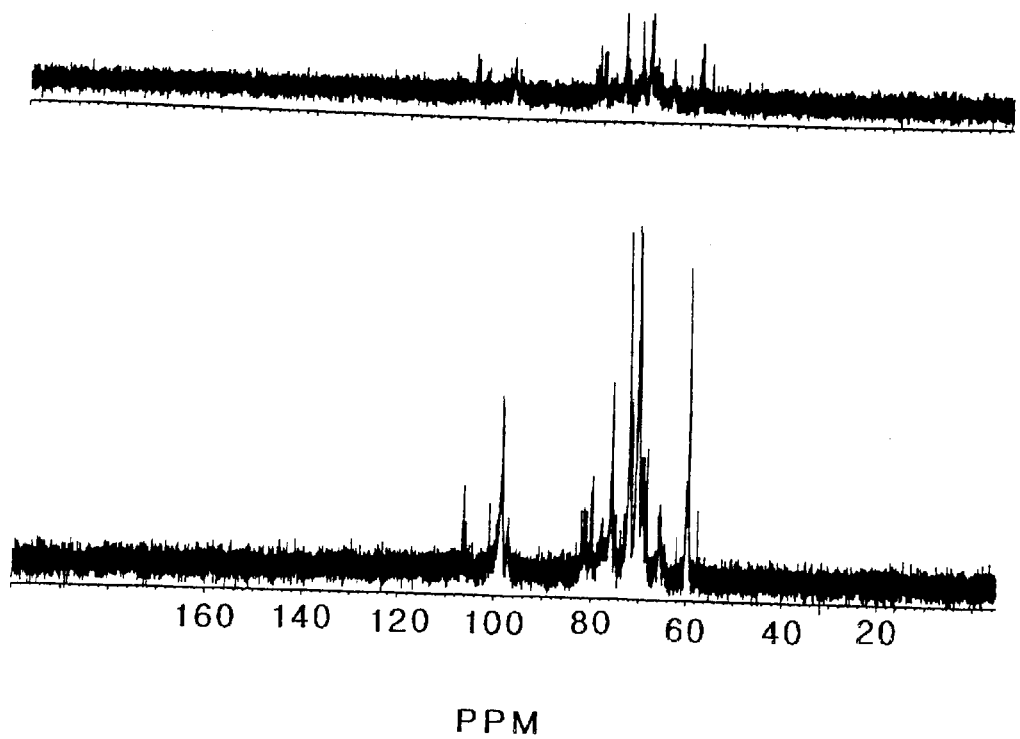
FIG. 3 depicts $^{13}$C-NMR scans of the arabinonmannan fractions 1 and 3.

All references cited herein are hereby incorporated in their entirety by reference.

The carbohydrate complex of the present invention, designated as Tubercin-5, is extracted from *M. tuberculosis*. Tubercin-5 is a mixture of polysaccharides having straight-chain and side-chain glycosidic bonds formed between such essential monosaccharides as mannose, arabinose, glucose and galactose. The molecular weight of said polysacchrides lies below 7,000, preferably in the range of 2,500 to 3,500 dalton.

Tubercin-5 of the present invention may be prepared as follows.

*M. tuberculosis* is, at first, cultured in a suitable medium, and the culture is diluted with water. The diluted culture is heated at a temperature range from 50 to 150° C., preferably from 110 to 130° C. under a pressure ranging from 10 to 30 psi, preferably from 15 to 20 psi. The medium suitable for the culture may be preferably Sauton's medium; and the water for dilution may be employed in an amount ranging from 10 to 30 folds, preferably, 20-fold volume of the culture. The heated culture is then allowed to remove bacterial residues therefrom. The removal of the bacterial residues may be conducted by a conventional method, e.g., using a centrifuge and/or a filter.

To the remaining culture solution is added an inorganic salt to form a protein precipitate. The inorganic salt which may be used in the present invention includes ammonium sulfate, sodium sulfate, sulfosalicylic acid and phosphotungstic acid, while sulfosalicylic acid and phosphotungstic acid are preferred. The inorganic salt may be employed to a final concentration ranging from 1 to 15 wt %, preferably from 8 to 10 wt %. Thereafter, from the resulting solution the precipitate therein is removed by a conventional method, e.g., a centrifugation. The remaining solution is then dialyzed against distilled water to remove the inorganic salt and to obtain a dialysis product. The removal process step may be repeated twice or more.

To the dialysis product is added an alcohol to obtain a precipitate, and the precipitate is washed with an alcohol-ether mixture. The alcohol which may be employed in the present invention includes ethanol, propanol and butanol, while ethanol is preferred. The ether may be preferably diethyl ether. The washed precipitate is then extracted with an organic solvent, e.g., phenol, diethyl ether or an alcohol, to remove lipid components therefrom. The extraction may be conducted in the presence of a buffer solution, e.g., a mixed solution of Tris-HCl buffer solution-EDTA.

Finally, the obtained precipitate is subjected to a purification step to obtain the carbohydrate complex of the present invention, designated as Tubercin-5. The purification may be carried out, e.g., by using an ion-exchange column chromatography.

Tubercin-5 thus obtained is a mixture of polysaccharides having an arabinomannan structure constructed from such monosaccharides as glucose(Glu), arabinose(Ara), galactose (Gal) and mannose(Man); and is made clear when it is subjected successively to per-O-methylation, hydrolysis, reduction, acetylation and GLC-MS analysis.

The structure of Tubercin-5 is further studied by examining the fragments obtained by the hydrolysis thereof. Namely, it can be shown by means of high performance anion exchange chromatography (HPAEC) that the hydrolysis product of Tubercin-5 is comprised of a number of monosaccharides and oligosaccharides of various chain lengths.

Four arabinomannan fractions obtained from the above chromatographic separation of the Tubercin-5 hydrolysis product are further analyzed by NMR. $^1$H-NMR results show the presence of α- or β-furanosyl and α-pyranosyl residues, while $^{13}$C-NMR data reveals that Tubercin-5 is possessive of: (1) a 5-linkage type α-Araf unit (residue), (2) a (3→5)-linkage type α-Araf unit substituted with a 5-linkage type α-Araf residue at the branching position, and (3) a disaccharide unit, β-Araf-(1→2)-α-Araf, as well as a di-substituted (3→5)-linkage type Araf unit.

For further structural analysis, Tubercin-5 is subjected successively to per-O-alkylation, partial hydrolysis and sodium borodeuteride (NaB[$^2$H]$_4$) reduction, and an FAB-MS analysis of the oligosaccharide alditol derivatives thus obtained shows the presence of simple (Man)$_2$ units as well as (Man)$_6$(Ara)$_6$(Glu)(Gal), (Man)$_9$(Ara)$_6$(Glu)(Gal) and other combinations of Man, Ara, Glu and Gal.

The above analyses show that the carbohydrate complex of the present invention, Tubercin-5, is comprised of polysaccharides having linear and branched chains of mannose, arabinose, glucose and galactose and having a molecular weight of 7,000 or less, preferably from 2,500 to 3,500. As noted above, higher molecular weight polysaccharides having the average molecular weight of, e.g., 12,000 or higher may induce undesirable side effects, e.g., hypersensitivity.

The carbohydrate complex of the present invention, Tubercin-5, is remarkably effective in treating various cancer patients, particularly those suffering from lung, stomach or uterine neck cancer. Tubercin-5 has an LD$_{50}$ value which is several orders of magnitude higher than the recommended dosage level. Accordingly, it is safe and nontoxic, has therapeutic effects on cancerous symptoms, increases the survival rate of the patients and eliminates or reduces the cancer tissues, all in the absence of any discernible adverse side effects.

Therefore, Tubercin-5 can be employed alone or in combination with other substances in a pharmaceutical composition for the treatment of cancers. The pharmaceutical composition of the present invention may comprise pharmaceutically acceptable excipients, carriers, diluents, lubricating agents, wetting agents and flavoring agents in combination with Tubercin-5. The inventive pharmaceutical composition may be prepared by employing any of the conventional methods known in the art.

The pharmaceutical composition comprising Tubercin-5 can be administered via a variety of routes including oral, transdermal, subcutaneous, intravenous and intramuscular introduction. In case a subcutaneous injection formulation is used, a typical daily dose of the active ingredient may range from about 0.001 to 1 μg/kg body weight, preferably from 0.01 to 0.5 μg/kg body weight. However, the dosage of the active ingredient may vary depending on various factors and a proper amount should be determined after evaluating the method of administration, the symptom as well as the age and weight of the patient, among others.

The following Examples are intended to further illustrate the present invention without limiting its scope.

Example 1

Preparation of Tubercin-5

*M. tuberculosis* (H$_{37}$R$_V$:ATCC 12301) was inoculated into a Sauton's medium [Sauton, B., *Internat. Cong. Appl. Chem.*, 19, 267–269(1912)] placed in a 250 ml flask and cultured for 4 weeks at 37° C. 300 g of the culture was diluted with about 6,000 g of water, and the diluted culture thus obtained was heated in an autoclave at 120° C. under a pressure of 16 psi.

The heated culture was centrifuged for 30 min. at 3,500–4,500 rpm, the supernatant was separated and filtered with a Seilg filter having a pore size of 0.1 μm. The solution thus obtained was filtered again using a Shämblan filter to remove remaining bacteria residues.

To the filtrate so obtained, sulfosalicylic acid was added to a concentration of 10 wt % and centrifuged to remove yellowish brown precipitates (proteins). The supernatant was placed in a semipermeable membrane bag (Thomas Co., U.S.A.) and dialyzed against distilled water for 3 days to remove sulfosalicylic acid.

The colloidal suspension in the membrane bag was concentrated, phosphotungstic acid was added thereto to a concentration of 7 wt %, and the protein precipitate formed therein was removed by centrifugation at 3,500 rpm for 20 min. The supernatant so obtained was placed in a semipermeable membrane bag and dialyzed against distilled water to remove inorganic salts present therein.

The dialysis solution was then diluted with a five-fold volume of ethanol and the resulting mixture was left standing at 4° C. for 24 hours to obtain a precipitate. The precipitate was washed twice with a ethanol-water(1:3) mixture, and to the washed precipitate was added a mixed solution of 20 mM Tris-HCl buffer(pH 83.0)–5 mM EDTA. The resulting mixture was extracted sequentially with a phenol, diethyl ether and ethanol to remove lipids present in the precipitate.

Finally, trace inorganic impurities were eliminated from the precipitate using a Bio-Gel P4 column (1.2×65 cm; Bio-Rad Laboratories, USA) to obtain 100 mg of the carbohydrate complex of the present invention, designated Tubercin-5.

Example 2

Structural Analysis of Tubercin-5

To analyze the monosaccharide constituents of Tubercin-5 prepared in Example 1, Tubercin-5 was dissolved in water to a concentration of 500 μg/ml and analyzed using the method developed by Oxford Glyco Systems of England using various monosaccharide standard solutions as references.

Tubercin-5 was subjected to a series of conventional reactions, i.e., per-O-methylation, acid-catalyzed hydrolysis, reduction and acetylalion to obtain per-O-trimethylsilyl (TMS) methylglycoside, and each component was identified with GLC-MS. Quantitative analysis of each TMS-methylglycoside was conducted using a flame ionization detector(FID), and the amounts of the glycosyl residues present in Tubercin-5 were determined, as shown in Tables 1 and 2.

TABLE 1

| Glycosyl Residue | Mole % |
|---|---|
| t-Araf | 9.4 |
| 2-Araf | 8.1 |
| 5-Araf | 44.1 |
| 3,5-Araf | 6.2 |
| 2,5-Araf | 0.1 |
| t-Manp | 2.2 |
| 4-Manp | 17.3 |
| 6-Manp | 4.1 |
| 2,6-Manp | 3.1 |
| t-Galf | 0.1 |
| 6-Galf | 2.0 |
| 2-Galf | 0.1 |
| 6-Glup | 3.2 |

TABLE 2

| Monosaccharide | Mole % |
|---|---|
| Arabinose | 67.9 |
| Mannose | 26.7 |
| Glucose | 3.2 |
| Galactose | 2.2 |

As shown in Tables 1 and 2, Tubercin-5, the carbohydrate complex of the present invention, is possessive of an arabinomannan structure, similar to those found in carbohydrate complexes of other tubercle bacilli. Further clarified by this study are the facts that the 4-mannopyranose (4-Manp) residue is present in Tubercin-5 and that the arabinose and mannose contents are much higher than the glucose and galactose contents.

Subsequent to the above analysis, 10 mg of Tubercin-5 was hydrolyzed in 6N HCl for 24 hrs. at 70° C., neutralized with 6 N NaOH and subjected to high performance anion exchange chromatography (HPAEC) usirng a CarboPac PA1 column (4×250 mm: Dionex) with a CarboPac PA guard column(3×25 mm) on Bio-LC equipped with a pulsed amperometric detector(Dionex), which employed a gold-plated electrode under the following condition:

sample size=26 μl pulse potential of pad, $E_1$=0.05 V $t_1$=480 ms $E_2$=0.06 V $t_2$=120 ms $E_3$=−80 V $t_3$=60 ms detector response time=1 sec eluent 1=1 M sodium acetate solution eluent 2=200 mM or 375 mM sodium hydroxide solution eluent 3=distilled water eluent gradient programs used:

(1) Program A
 eluent 1: 5% at 0 min., 50% at 45 min.
 eluent 2(200 mM NaOH): 50% at 0 to 45 min.

(2) Program B
 eluent 1: 5% at 0 min., 15% at 5 min., 25% at 20 min., 35% at 45 min. and 45% at 65 min.
 eluent 2(375 mM NaOH): 40% at 0–65 min.

eluent flow rate=1 ml/min.

The observed peak responses were calibrated using standard solutions containing known amounts of reference compounds.

The Bio-LC scan of the hydrolysis products of Tubercin-5, as was defined by the pulsed amperometric detector, is shown in FIG. 1. Tubercin-5 is, as the scan in FIG. 1 suggests, a mixture of polysaccharides having various monosaccharide constituents and different chain lengths. This hydrolysis mixture was divided into four fractions and each was analyzed as follows;

Each of the four arabinomannan fractions was dissolved in 1 ml of $^2H_2O$, added 1 μl of acetone as an internal standard and subjected to NMR analyses(Bruker ACE-300). A $^{13}C$-NMR scan showed a peak at δ 31.4 relative to the acetone standard, while $^1H$-NMR exhibited a peak at δ 2.04 relative to the acetone peak. The $^1H$-NMR scans of arabinomanan fraction 1, 2, 3, and 4 of Tubercin-5 are reproduced in FIG. 2, which shows the presence of saccharide chain residues in fractions 1 and 3 (the peaks marked b,y arrows in the scans for fractions 1 and 3 are identified to be the H-1 signal of a β-glycosyl residue). Other protons of each of the polysaccharides show peaks at δ 5.0–4.5 and these correspond to the α- or β-furanosyl as well as α-pyranosyl residues.

The $^{13}C$-NMR scans of fractions 1 and 3 of Tubercin-5 of the present invention are illustrated in FIG. 3. Based on the known results for the soluble arabinonmannan component present in *M. tuberculosis* [Daffe, M. et al., *J. Biol. Chem.*, 265, 6734–6743(1990)], the chemical shift of the non-reducible terminus of the arabinan chain can be deduced. It has thus been found that the terminal t-β-Araf (C-1, δ 101–102) is bonded to the 2-position of α-Araf (C-1, δ 106–108) and that this disaccharide is in turn bonded to the 3- and 5-positions of α-Araf residue. The remaining Ara and Man residues were confirmed to be of the furanoid nature based on the chemical shift values (δ 107–109). Namely, the chemical shift values for C-1 of t-β-Araf and 2-linkage type α-Araf, C-2 of arabinose residue and C-5 of t-β-Araf reported in the literature cited above are very close to those observed in this study. In case of the furanosyl residue, the available data for 2-, 3- and 5-linkage type Araf residues and those for 5-Galf residue were relied upon in elucidating the fact that the C-1 peak appearing at δ 108–109 is mostly due to the α-Araf/β-Galf units [Gorin, P. A. J. et al., *Carbohydrate Res.*, 48, 171–186(1976); Joseleau, J. P. et al., *Carbohydrate Res.*, 58, 165–175(1977); Mizutani, K. et al., *Carbohydrate Res.*, 185, 27–38(1989)]. The close similarity observed in the $^{13}C$-NMR data for the two soluble arabinomannan components of the cell wall of *M. tuberculosis* suggests that these components have similar structural features. It was shown that said structural features can be expressed as follows:

(a) 5-linkage type α-Araf residue;

(b) branched (3→5) linkage type α-Araf unit substituted with 5-linkage type α-Araf residue at the branching position; and (c) disaccharide β-Araf(1→2)-α-Araf and (3→5) linkage type α-Araf units.

In order to analyze the arabinomannan component in more detail, a per-O-methylated arabinomannan fraction was treated with 1M CF$_3$COOH at 75° C. for an hour to perform partial hydrolysis thereof, and the resulting material was reduced using NaB[$^2$H]$_4$ to obtain oligosaccharide alditol derivatives, which were then converted to per-O-alkylated oligosaccharide alditols to be subjected to FAB-MS analysis.

Figure 4:
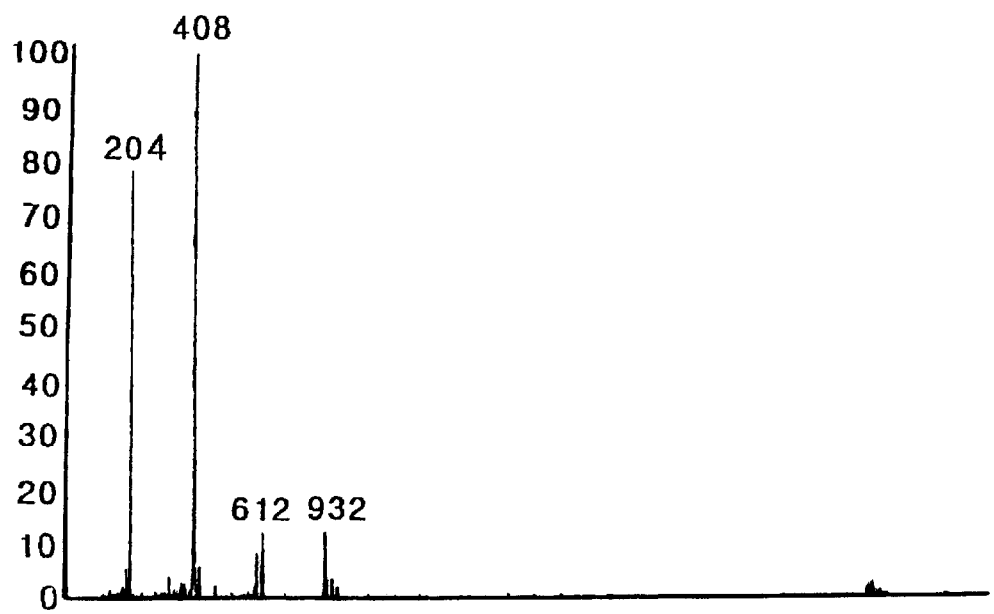
FIG. 4 illustrates the result of FAB-MS analysis of oligosaccharide alditol derivatives of the arabinomannan component of Tubercin-5.
Figure 4:
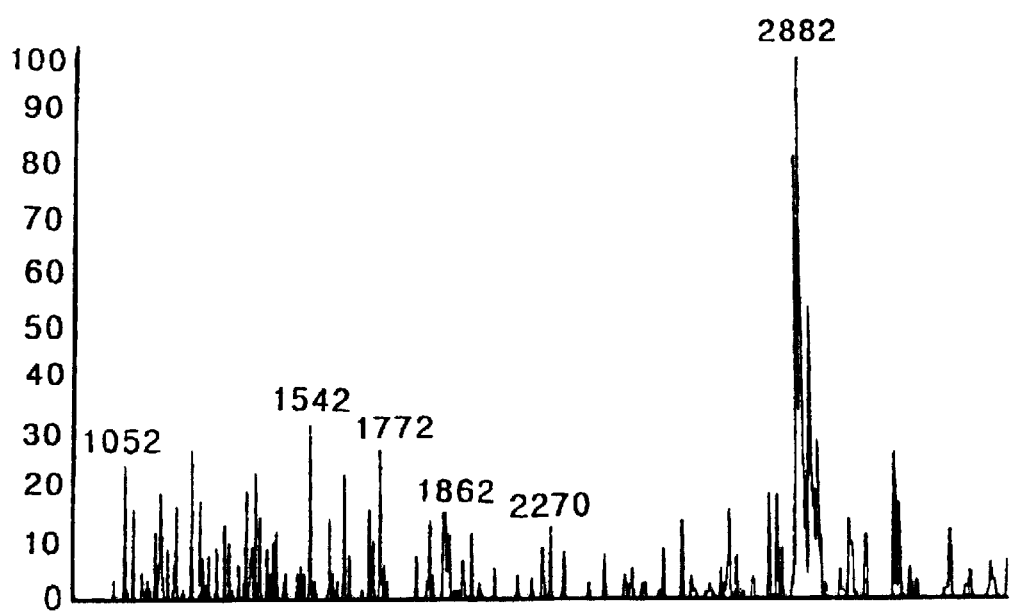

FIG. 4 shows the result of FAB-MS analysis of the positive ions of the oligosaccharide alditols derived from Tubercin-5 and one can see the intense molecular ion peaks corresponding to [M+Na]$^+$ and [M+NH$_4$]$^+$, wherein the peaks at 408, 612, 932, 1862, 2270 and 2882 are assigned to (Man)$_2$, (Man)$_3$, (Man)$_3$(Ara), (Man)$_4$(Ara)$_6$, (Man)$_6$(Ara)$_6$(Glu)(Gal) and (Man)$_9$(Ara)$_9$(Glu)(Gal), respectively.

The structures of the above fragments are shown in Table 3.

TABLE 3

| Molecular ion N + Na (m/z) | Structure |
| --- | --- |
| 408 | Man-Man |
| 612 | Man-Man-Man |
| 932 | Man-Man-Man-Ara |
| 1052 | Man-Man-Man-Ara-Ara |
| 1542 | Man-Man-Man-Man-Ara-Ara-Ara-Ara |
| 1722 | Man-Man-Man-Ara-Ara-Ara-Ara-Ara-Ara |
| 1862 | Man-Man-Man-Man-Ara-Ara-Ara-Ara-Ara-Ara |
| 2066 | Man-Man-Man-Man-Man-Ara-Ara-Ara-Ara-Ara-Ara |
| 2270 | Man-Man-Man-Ara-Ara-Ara----X<br>Man-Man-Man-Ara-Ara-Ara---\| |
| 2882 | Man-Man-Man-Ara-Ara-Ara----X<br>Man-Man-Man-Ara-Ara-Ara---\|<br>Man-Man-Man-Ara-Ara-Ara---\| |

*--- indicates the presence of continuous arabinose residues, and X indicates the presence of glucose and galactose residues in polysaccharides having a molecular weight of more than 3,000. Polysaccharides having a molecular weight greater than 3,500 constitute less than 10% of the total polysaccharides.

Test Example 1

Acute Toxicity of Tubercin-5 to Rats and Mice

Tubercin-5 prepared in Example 1 was dissolved in physiological saline to a concentration of 2 mg/ml, various amounts of which were administered to 6-week old mice (ICR mice: 20–25 g) and rats (SD rat: 150 g) by way of intravenous or subcutaneous injections to observe the fatality thereof. The results are shown in Table 4.

TABLE 4

| Test animal | Injection | Sex & Heads | | Dosage (mg/kg) | Fetality | LD$_{50}$ (mg/kg) |
| --- | --- | --- | --- | --- | --- | --- |
| Mice | Venous | F | 6 | 0 | 0/6 | >20 |
| | | F | 6 | 10 | 0/6 | |
| | | F | 6 | 20 | 0/6 | |
| | | M | 6 | 0 | 0/6 | >20 |
| | | M | 6 | 10 | 0/6 | |
| | | M | 6 | 20 | 0/6 | |
| | Subcutaneous | F | 6 | 0 | 0/6 | >50 |
| | | F | 6 | 25 | 0/6 | |
| | | F | 6 | 50 | 0/6 | |
| | | M | 6 | 0 | 0/6 | >50 |
| | | M | 6 | 25 | 0/6 | |
| | | M | 6 | 50 | 0/6 | |
| Rats | Venous | F | 6 | 0 | 0/6 | >20 |
| | | F | 6 | 10 | 0/6 | |
| | | F | 6 | 20 | 0/6 | |
| | | M | 6 | 0 | 0/6 | >20 |
| | | M | 6 | 10 | 0/6 | |

TABLE 4-continued

| Test animal | Injection | Sex & Heads | | Dosage (mg/kg) | Fetality | LD$_{50}$ (mg/kg) |
| --- | --- | --- | --- | --- | --- | --- |
| | | M | 6 | 20 | 0/6 | |
| | Subcutaneous | F | 6 | 0 | 0/6 | >50 |
| | | F | 6 | 25 | 0/6 | |
| | | F | 6 | 50 | 0/6 | |
| | | M | 6 | 0 | 0/6 | >50 |
| | | M | 6 | 25 | 0/6 | |
| | | M | 6 | 50 | 0/6 | |

The results in Table 4 show that regardless of the test animal used, the LD$_{50}$ value of Tubercin-5 is more than 20,000 µl/kg in cases of intravenous injections, while it is above 50,000 µg/kg when administered by subcutaneous injections. Accordingly, considering that an effesctive daily dosage of Tubercin-5 for a human patient may range from about 0.001 to 1 µg/kg, preferably from 0.01 to 0.5 µg/kg of the body weight, Tubercin-5 is essentially non-toxic.

The test animals subjected to the above treatments were examined over a period of 14 days to measure the weight changes, and then were sacrificed to examine the liver, kidney, spleen, stomach, lung and heart tissues thereof. Also, each of the organ samples was fixed in a 10% formaldehyde solution to prepare a pathology specimen, which was stained with hematoxvlin-eosin and examined with a microscope. No abnormalities were detected in any of the specimens examined.

Test Example 2

The Effect of the Combined use of Tubercin-5 and Cyclophosphamide 56 white male mice each weighing about 22 g (ICR mice: 20–25 g) were divided into 7 groups, and each mouse was administered, by a subcutaneous injection in its abdominal section, 0.2 nm of 10% Ehrlich ascites tumor cell solution (1.4×10$^7$ cells) in accordance with the method of Baillif [Baillif, R. N., *Caner Research*, 15, 554–558(1954)]. Subsequently, each mouse was subjected to one of the following treatments:

Control Group: abdominal injection of 0.2 ml of 0.9% physiological saline;

Group 1: subcutaneous injection of a 1 µg/ml Tubercin-5 solution in 0.9% physiological saline;

Group 2: subcutaneous injection of a 2 µg/ml Tubercin-5 solution in 0.9% physiological saline;

Group 3: intraperitoneal injection of 0.55 mg (corresponding to 25 mg per kg of body weight) of cyclophosphamide dissolved in 0.2 ml of water;

Group 4: intraperitoneal injection of 1.1 mg (corresponding to 50 mg/kg body weight) of cyclophosphamide dissolved in 0.2 ml of water;

Group 5: intraperitoneal injection of 0.55 mg of cyclophosphamide coupled with subcutaneous injection of 1 µg of Tubercin-5; and Group 6: intraperitoneal injection of 1.1 mg of cyclophosphamide coupled with subcutaneous injection of 1 µg of Tuercin-5.

Each of the above injections treatments was repeated 6 times over a period of 6 days. Fifteen days after the initial inoculation with cancer cells, each of the mice so treated was anesthetized with diethyl ether and killed. The solid tumor growing in the abdominal section was carefully isolated from other organ tissues, cleaned using filter papers and weighed. For each group, the average weight of the cancerous tissue was tabulated and evaluated by the t-test, the results of which are shown in Table 5.

TABLE 5

| Group* | Average weight of cancer tissue (av. wt. ± std. dev.) | Relative weight |
|---|---|---|
| Control | 3.25 ± 0.12 | 100 (ref) |
| 1 | 2.35 ± 0.06 | 72.3 |
| 2 | 2.25 ± 0.05 | 69.2 |
| 3 | 2.32 ± 0.05 | 71.3 |
| 4 | 2.15 ± 0.04 | 66.1 |
| 5 | 1.51 ± 0.03 | 46.4 |
| 6 | 1.10 ± 0.02 | 33.8 |

*Each group contained 8 mice

As the data in Table 5 suggest, the administration of cyclophosphamide or Tubercin-5 alone produced anticancer effects of similar magnitude, while the combined use of cyclophosphamide and Tubercin-5 resulted in a marked decrease in the cancerous growth. This result demonstrates the usefulness of Tubercin-5 in cancer therapies, particularly when it is combined with one or more of other existing anticancer agents.

As in the above examples, Tubercin-5 of the present invention is an extraordinarily effective anticancer agent that is safe to use without any adverse side effects.

While the invention has been described with respect to the above specific embodiments, it should be recognized that various modifications and alterations which may be apparent to those skilled in the art to which the invention pertains may be made and also fall within the scope of the invention as defined by the claims that follow.

What is claimed is:

1. An extract of *Mycobacterium tuberculosis* consisting essentially of polysaccharides comprising mannose, arabinose, glucose and galactose as constituents thereof, wherein the weight average molecular weight of each polysaccharide is 7,000 or less and the partial acid hydrolysis product of the polysaceharides comprises:

Man-Man-Man-Ara-Ara-Ara-$(Ara)_n$ ⎤
Man-Man-Man-Ara-Ara-Ara-$(Ara)_o$ ⎬—X; and
Man-Man-Man-Ara-Ara-Ara-$(Ara)_p$ ⎦

Man-Man-Man-Man-Man-Ara-Ara-Ara-Ara-Ara-Ara;

wherein n, o and p are individually an integer; and x is a chain of glucose and galactose residues.

2. The extract of claim 1, wherein the partial acid hydrolysis product further comprises:

Man-Man-Man-Ara-Ara-Ara-$(Ara)_l$ ⎤
Man-Man-Man-Ara-Ara-Ara-$(Ara)_m$ ⎦—X wherein l and m are individually an integer; and x is a zhain of glucose and galactose residues.

3. The extract of claim 2, wherein the partial acid hydrolysis product comprises:

Man-Man-Man-Ara-Ara-Ara ⎤
Man-Man-Man-Ara-Ara-Ara ⎦—Glu-Gal; and

Man-Man-Man-Ara-Ara-Ara ⎤
Man-Man-Man-Ara-Ara-Ara ⎬—Glu-Gal.
Man-Man-Man-Ara-Ara-Ara ⎦

4. The extract of claim 1, wherein the partial acid hydrolysis product further comprises:

Man-Man;
Man-Man-Man;
Man-Man-Man-Ara;
Man-Man-Man-Ara-Ara;
Man-Man-Man-Man-Ara-Ara-Ara-Ara;
Man-Man-Man-Ara-Ara-Ara-Ara-Ara-Ara; and
Man-Man-Man-Man-Ara-Ara-Ara-Ara-Ara-Ara.

5. The extract of any one of claims 1 to 4, wherein most of the polysaccharides have a weight average molecular weight ranging from 2,500 to 3,500.

6. A pharmaceutical composition for treating a cancerous symptom comprising a therapeutically effective amount of the extract of any one of claims 1 to 4 and a pharmaceutically acceptable carrier.

7. A process for the preparation of the polysaccharide complex defined in claim 1, comprising the steps of:

(a) culturing *Mycobacterium tuberculosis* in a medium, heating the culture diluted with water at a temperature ranging from 50 to 150° C. under a pressure ranging from 10 to 30 psi and removing bacterial residues from the heated culture solution;

(b) adding an inorganic salt to the remaining solution to form a precipitate and removing the precipitate from the resulting solution;

(c) dialyzing the remaining solution to obtain a dialysis product;

(d) adding an alcohol to the dialysis product to obtain a precipitate, washing the precipitate with an alcohol-ether mixture and extracting the washed precipitate with an organic solvent; and (e) purifying the extract to obtain the polysaccharide complex.

8. The process of claim 7, wherein the inorganic salt is sulfosalicylic acid or phosphotungstic acid.

* * * * *